United States Patent [19]

Lepage et al.

[11] Patent Number: 4,567,286

[45] Date of Patent: Jan. 28, 1986

[54] PREPARATION OF HYDROGENATED SILANES BY REDISTRIBUTION OF HYDROSILANES

[75] Inventors: Jean-Luc Lepage, Sainte-Foy-Les-Lyon; Gerard Soula, Meyzieu, both of France

[73] Assignee: Rhone-Poulenc Specialites Chimiques, Courbevoie, France

[21] Appl. No.: 655,722

[22] Filed: Sep. 28, 1984

[30] Foreign Application Priority Data

Sep. 28, 1983 [FR] France ................................ 83 15403

[51] Int. Cl.$^4$ ............................ C07F 7/08; C07F 7/12
[52] U.S. Cl. ..................................................... 556/469
[58] Field of Search ........................................... 556/469

[56] References Cited

U.S. PATENT DOCUMENTS 2,732,282 1/1956 Bailey et al. ..................... 556/469 X
2,834,648 5/1958 Bailey et al. ..................... 556/469 X
3,627,501 12/1971 Kruger ............................ 556/469 X
3,769,310 10/1973 Viego et al. ........................ 556/469
4,405,590 9/1983 Simon et al. .................... 556/469 X

*Primary Examiner*—Paul F. Shaver
*Attorney, Agent, or Firm*—Burns, Doane, Swecker & Mathis

[57] ABSTRACT

Hydrogenosilanes are facilely prepared by redistribution, by reacting (1) a silane having the formula $H_mSiX_{4-m}$ in which X is halogen or an alkoxy group and m is an integer equal to 0, 1, 2, or 3, with (2) an alkyl or aryl hydrogenosilane having the formula $R_nH_pSiX'_{4-(n+p)}$ in which X' is halogen or an alkoxy group, R is at least one alkyl or aryl group, which may be identical or different, and n and p, which may be identical or different, are integers equal to 1, 2 or 3, with the proviso that $n+p \leq 4$, in the presence of (3) a catalytically effective amount of a catalyst system which comprises (i) at least one ionic inorganic salt having the formula $M^+A^-$ and (ii) a compound which complexes the $M^+$ cation of said salt (i) and at least partially solubilizes and dissociates same in the medium of reaction.

20 Claims, No Drawings

PREPARATION OF HYDROGENATED SILANES BY REDISTRIBUTION OF HYDROSILANES

BACKGROUND OF THE INVENTION

1. Field of the Invention

The present invention relates to the preparation of hydrogenated silanes by redistribution, and, more especially, to the preparation of a silane containing at least one Si—H bond by reacting a less hydrogenated or non-hydrogenated silane with an alkyl or aryl hydrogenosilane in the presence of a catalyst system.

2. Description of the Prior Art

It is known to this art to prepare silanes containing at least two Si—H bonds by dismutation of two molecules of a hydrogenosilane optionally comprising alkyl or aryl groups. Thus, French Pat. Nos. 2,096,605, 2,118,725, 2,261,977, 2,290,447, and 2,290,448 describe such dismutation reactions in the presence of various catalysts, wherein such dismutation reactions can be represented as follows:

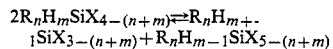

in which n denotes an integer equal to 0, 1 or 2; m denotes an integer equal to 1, 2 or 3 with $n+m \leq 3$, and R denotes an alkyl or aryl group and X a halogen It is also known to prepare alkyl or aryl hydrogenosilanes by redistribution between a molecule of a hydrogenosilane and a molecule of alkyl or aryl halosilane. The described catalysts for these redistribution reactions are notably those which are the subject of French Pat. Nos. 1,603,167, 2,290,447, 2,467,855, 2,290,448, 2,096,605 and 2,119,477, wherein such redistribution reactions can be represented as follows:

$$H_mSiX_{4-m} + R_nSiX_{4-n} \rightarrow H_{m-1}SiX_{5-m} + R_nHSiX_{3-n}$$

in which m denotes an integer equal to 1, 2, 3 or 4 and n denotes an integer equal to 1, 2 or 3 and R denotes an alkyl or aryl group and X a halogen.

SUMMARY OF THE INVENTION

A major object of the present invention is the provision of an improved process for the preparation of a hydrogenosilane by a novel redistribution reaction between a silane which is less hydrogenated than that sought to be produced or is non-hydrogenated, and an alkyl or aryl hydrogenosilane, in the presence of a catalytic system, and wherein such reaction can be represented as follows:

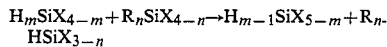

in which R denotes an alkyl or aryl group, X and X', which may be identical or different, denote a halogen or an alkoxy group, m denotes an integer equal to 0, 1, 2 or 3; n and p, which may be identical or different, denote integers equal to 1, 2 or 3 with $n+p \leq 4$.

The improved process according to this invention makes it possible to prepare hydrogenosilanes which are more fully hydrogenated than the beginning or starting material silane, with conversions which are much higher than those obtained when such desired final products are produced by dismutation; it moreover makes it possible to commercialize byproducts obtained during the direct synthesis of methyl chorosilanes, such as methyldichlorosilane. Further, the process according to the invention is particularly suitable for the preparation of trichlorosilane, dichlorosilane and/or silane according to the reactions:

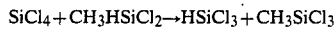

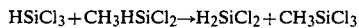

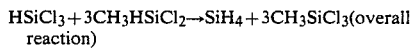

The process according to the invention thus also makes it possible to produce raw materials which permit easy access to silicon of photovoltaic or electronic quality. It also permits the commercialization of tetrachlorosilane, a byproduct of the manufacture of silicon of photovoltaic or electronic quality, by cracking trichlorosilane. Tetrachlorosilane is thus valorized by conversion to trichlorosilane and/or dichlorosilane under conditions which are notably economical when compared to those known from the literature.

Briefly, the present invention features a process for the preparation of a hydrogenosilane via redistribution, by reaction (1) a silane having the formula $H_mSiX_{4-m}$ in which X denotes a halogen or an alkoxy group and m denotes an integer equal to 0, 1, 2 or 3, with (2) an alkyl or aryl hydrogenosilane having the formula $R_nH_pSiX'_{4-(n+p)}$ in which X' denotes a halogen or an alkoxy group, R denotes an alkyl or aryl group and n and p, which may be identical or different, denote integers equal to 1, 2 or 3 with $n+p \leq 4$; in the presence of a catalytically effective amount of (3) at least one ionic inorganic salt of the formula $M^+A^-$ together with at least one complexing agent which at least partially solubilizes said salt in the reaction medium by complexing the cation $M^+$ thereof and at least partially dissociating said salt; and thereafter recovering the hydrogenosilane or hydrogenosilanes thus formed.

DETAILED DESCRIPTION OF THE INVENTION

More particularly according to the present invention, the silanes which are used are preferably those having the formula $H_mSiX_{4-m}$ in which X denotes a halogen or alkoxy group and m an integer equal to 0, 1, 2 or 3. In a preferred embodiment of the invention, tetrachlorosilane, trichlorosilane, dichlorosilane, or admixture thereof, are used.

The alkyl or aryl hydrogenosilanes which are employed in the process of the invention are those which have the formula $R_nH_pSiX'_{4-(n+p)}$ in which X' denotes a halogen or an alkoxy group, R denotes at least one alkyl or aryl group which may be identical or different and n and p, which may be identical or different, denote integers equal to 1, 2 or 3 with $n+p \leq 4$.

In another preferred embodiment of the invention, methylsilane, methylchlorosilane, dimethylchlorosilane, methyldichlorosilane, dimethylsilane, trimethylsilane, phenyldichlorosilane, phenylchlorosilane, diphenylchlorosilane, ethyldichlorosilane, methylphenylchlorosilane, methylphenylsilane, or admixtures thereof, are used.

The ionic inorganic salts $M^+A^-$ comprising the catalyst system according to the invention are unreactive towards the silanes present in the reaction medium and are preferably selected from among those in which $M^+$ is an alkali metal, an alkaline earth metal or ammonium, and more preferably $M^+$ is $Li^+$, $Na^+$, $K^+$, $Ca^{++}$ and/or $NH_4^+$, and $A^-$ is preferably halogen, $SCN^-$, $CN^-$ and/or $CO_3^=$, more preferably $Cl^-$, $Br^-$, $I^-$ and/or $F^-$.

While not wishing to be bound by or to any particular theory, it would appear that the surprising results afforded by the present invention are attributable to the fact that the agent or compound which complexes the $M^+$ cation of the ionic inorganic salt effects the at least partial solubilization and dissociation thereof in the reaction medium, whereby the catalytic activity of the anion $A^-$ is greatly increased.

In a preferred embodiment of the invention, the compound which complexes the cation of the ionic inorganic salt is a sequestering agent of the formula:

$$[N-(CHR_1-CHR_2-O-(CHR_3-CHR_4-O)_n-R_5)_3] \quad (I)$$

in which n is an integer greater than or equal to 0 and less than or equal to 10 ($0 \leq n \leq 10$), $R_1$, $R_2$, $R_3$ and $R_4$, which may be identical or different, denote a hydrogen atom or an alkyl radical containing from 1 to 4 carbon atoms and $R_5$ denotes an alkyl or cycloalkyl radical containing from 1 to 12 carbon atoms, a phenyl radical or a $-C_mH_{2m}-\phi$ or $C_mH_{2m+1}-\phi-$ radical, where m ranges from 1 to 12 ($1 \leq m \leq 12$), and $\phi$ is benzene.

In a second preferred embodiment of the invention, the complexing compound is a macrocyclic polyether containing from 15 to 30 ring atoms and comprising 4 to 10 —O—X units in which X is either $-CHR_6-CHR_7-$ or $-CHR_6-CHR_8-CR_9R_7-$, $R_6$, $R_7$, $R_8$ and $R_9$, which may be identical or different, being a hydrogen atom or an alkyl radical containing from 1 to 4 carbon atoms, one of the symbols X optionally being $-CHR_6-CHR_8-CR_9R_7-$ when the —O—X units comprise the group $-O-CHR_6-CHR_7-$.

In a third preferred embodiment of the invention, the complexing compound is a macrocyclic or dicyclic compound of the general formulae IIa or IIb:

in which Y denotes N or P; A denotes an alkylene group containing from 1 to 3 carbon atoms; D denotes O, S or $N-R_{11}$ where $R_{11}$ denotes an alkyl radical containing from 1 to 6 carbon atoms; $R_{10}$ denotes an alkyl radical containing from 1 to 6 carbon atoms; and p, q and r, which may be identical or different, are integers ranging from 1 to 5.

In a fourth preferred embodiment of the invention, a mixture of at least two of the aforesaid complexing compounds is used.

And in a fifth preferred embodiment of the invention, the complexing compound is selected from among sequestering agents, macrocyclic polyethers (also designated "crown ethers") and macrocyclic or dicyclic compounds (also designated "cryptants"), grafted onto cross-linked organic polymer supports. These grafted complexing compounds are advantageously those described in published European Patent Application No. 46,706 in the case of the grafted sequestering agents and in the *Angew. Chem.*, Int. Ed., Engl., 18, 421–429 (1979) in the case of crown ethers or grafted cryptants.

The grafted sequestering agents described in published European Patent Application No. 46,706 are characterized in that they comprise a cross-linked organic polymer support and a plurality of functional groups bonded to said support, and having the general formula:

$$N \begin{cases} (CHR'_1-CHR'_2-O)_{\overline{n'}} \\ (CHR'_3-CHR'_4-O)_{\overline{m'}}-R'_5 \\ (CHR'_6-CHR'_7-O)_{\overline{p'}}-R'_8 \end{cases} \quad (III)$$

in which $R'_1$, $R'_2$, $R'_3$, $R'_4$, $R'_6$ and $R'_7$, which may be identical or different, are each a hydrogen atom or an alkyl radical containing from 1 to 4 carbon atoms, $R'_5$ and $R'_8$, which may be identical or different, denote a hydrogen atom, an alkyl or cycloalkyl radical containing from 1 to 12 carbon atoms, a phenyl radical, a $-C_{q'}H_{2q'}-\phi-$ or $C_{q'}H_{2q'+1}-\phi-$ radical with $q'$ greater than or equal to 1 and less than or equal to approximately 12, and in which n', m', and p', which may be identical or different, are greater than or equal to 1 and less than or equal to 10.

In another preferred embodiment of the invention, a sequestering agent of the formula (I) is employed, in which $R_1$, $R_2$, $R_3$ and $R_4$ denote a hydrogen atom or a methyl radical, with $R_5$ and n being as above defined.

Exemplary such sequestering agents are:

[1] tris(3-oxabutyl)amine of the formula:

$$N-CH_2-CH_2-O-CH_3)_3$$

[2] tris(3,6-dioxaheptyl)amine of the formula:

$$N-CH_2-CH_2-O-CH_2-CH_2-O-CH_3)_3$$

[3] tris(3,6,9-trioxadecyl)amine of the formula:

$$N-CH_2-CH_2-O-CH_2-CH_2-O-CH_2-CH_2-O-CH_3)_3$$

[4] tris(3,6-dioxaoctyl)amine of the formula:

$$N-CH_2-CH_2-O-CH_2-CH_2-O-C_2H_5)_3$$

[5] tris(3,6,9-trioxaundecyl)amine of the formula:

$$N-CH_2-CH_2-O-CH_2-CH_2-O-CH_2-CH_2-O-C_2H_5)_3$$

[6] tris(3,6-dioxanonyl)amine of the formula:

$$N-CH_2-CH_2-O-CH_2-CH_2-O-C_3H_7)_3$$

[7] tris(3,6,9-trioxadodecyl)amine of the formula:

N—CH$_2$—CH$_2$—O—CH$_2$—CH$_2$—O—CH$_2$—CH$_2$—O—C$_3$H$_7$)$_3$

[8] tris(3,6-dioxadecyl)amine of the formula:

N—CH$_2$—CH$_2$—O—CH$_2$—CH$_2$—O—C$_4$H$_9$)$_3$

[9] tris(3,6,9-trioxatridecyl)amine of the formula:

N—CH$_2$—CH$_2$—O—CH$_2$—CH$_2$—O—CH$_2$—CH$_2$—O—C$_4$H$_9$)$_3$

[10] tris(3,6,9,12-tetraoxatridecyl)amine of the formula:

N—CH$_2$—CH$_2$—O—CH$_2$—CH$_2$—O)$_3$—CH$_3$)$_3$

[11] tris(3,6,9,12,15,18-hexaoxanonadecyl)amine of the formula:

N—CH$_2$—CH$_2$—O—(CH$_2$—CH$_2$—O—$_5$CH$_3$)$_3$

[12] tris(3,6-dioxa-4-methylheptyl)amine of the formula:

N—CH$_2$—CH$_2$—OCH—CH$_3$—CH$_2$—O—CH$_3$)$_3$

[13] tris(3,6-dioxa-2,4-dimethylheptyl)amine of the formula:

N—CH$_2$CH—CH$_3$)—OCH(CH$_3$)—CH$_2$—O—CH$_3$)$_3$.

The amines which may be used are per se known to the prior art. Thus, French Pat. No. 1,302,365 describes the tertiary amines N—CH$_2$—CH$_2$—O—CH$_3$)$_3$ and N—CH$_2$—CH$_2$—O—CH$_2$—CH$_2$—O—CH$_3$)$_3$ prepared as byproducts of the synthesis of the corresponding primary and secondary amines, such primary and secondary amines being products useful as intermediates in the synthesis of pharmaceutical substances, corrosion inhibitors, intermediates for the synthesis of chemical products for agricultural purposes, and as emulsifiers. It will of course be appreciated that the field of application of the amines obtained in the aforesaid French Pat. No. 1,302,365, which may be the same as the amines employed in the process of the present application, is completely remote from the use intended herein.

The macrocyclic polyethers which may be used in the process of the invention are known under the general name of "crown ethers" and are described in French Patent Application No. 69/43,879 published under No. 2,026,481.

As examples of the crown ethers which may be used consistent herewith, representative are:

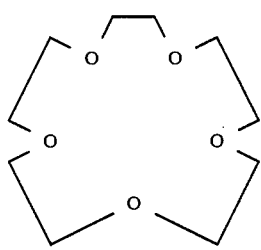

The macrocyclic and dicyclic compounds are described in French Patent Application No. 70/21,079 published under No. 2,052,947. As examples of such compounds useful according to this invention, representative are:

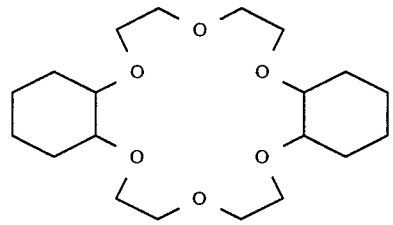

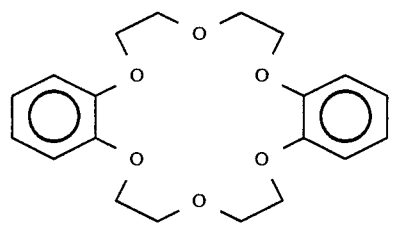

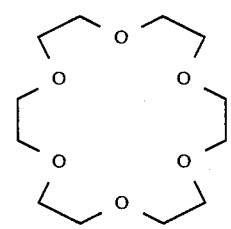

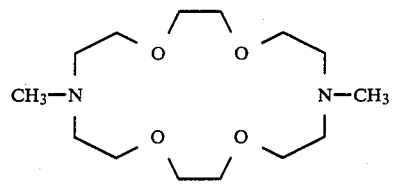

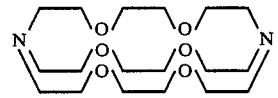

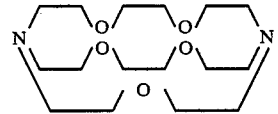

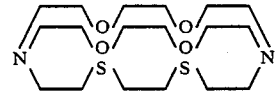

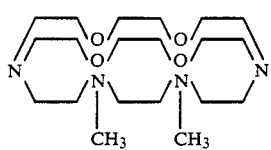

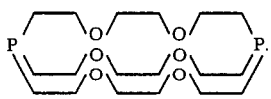

In another preferred embodiment of the invention, a supported sequestering agent is used comprising a cross-linked organic polymer support with a plurality of functional groups bonded to said support, having the general formula (III), in which $R'_1$, $R'_2$, $R'_3$, $R'_4$, $R'_6$ and $R'_7$, which may be identical or different, denote a hydrogen atom or the methyl radical and $R'_5$ and $R'_8$, which may be identical or different, denote a hydrogen atom or an alkyl radical containing from 1 to 4 carbon atoms. And in still another preferred embodiment of the invention, n', m' and p', which may be identical or different, are greater than or equal to 1 and less than or equal to 6.

Exemplary of such functional groups, those having the following formulae are representative:

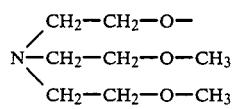

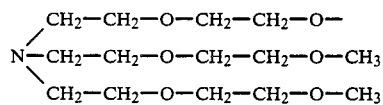

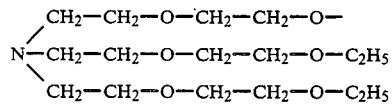

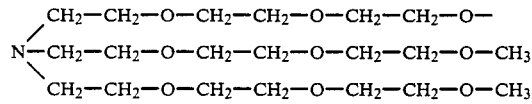

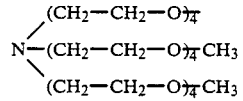

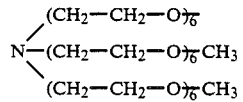

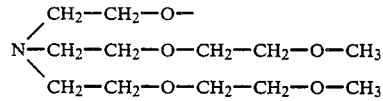

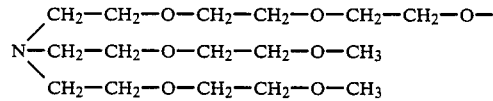

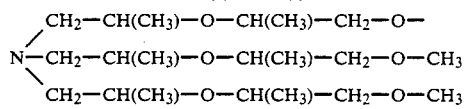

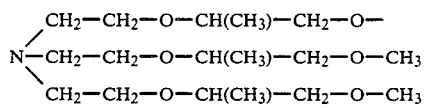

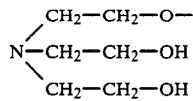

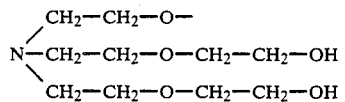

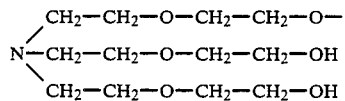

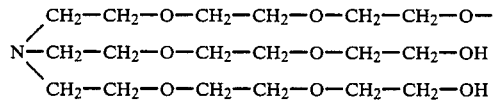

or

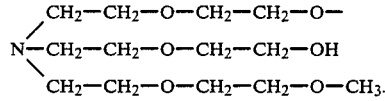

The support may be derived from any cross-linked organic polymer containing groups which are capable of being substituted with the functional groups of the formula (III).

Exemplary of organic polymers suitable for the present invention are polymers derived from vinylaromatic compounds, such as styrene and methylstyrene, and copolymers of vinylaromatic compounds and $C_4$-$C_6$ conjugated dienes, such as copolymers of styrene with butadiene and styrene with isoprene.

It is especially preferred consistent herewith to use polystyrene as the organic polymer, with the cross-linking agent therefor, also preferably, being divinylbenzene. The degree of cross-linking is an important factor. It is necessary, in fact, that the functional groups of the formula (III) grafted onto the polystyrene be active. For this, it is necessary that the molecules of the solvent in which the supported sequestering agent is to be employed, for those applications below described, penetrate inside the polymer. For this purpose, it is necessary that the degree of cross-linking should not be too high, such as not to prevent the entry of the solvent and reactants. It is preferred to employ a polystyrene whose degree of cross-linking with divinylbenzene is below approximately 10%. Still more preferably, the degree of cross-linking is below approximately 5%.

The group which may be substituted is preferably the chlorine or bromine atom in the chloromethyl —$CH_2Cl$ or bromomethyl —$CH_2Br$ substituent on the benzene ring of the polystyrene.

It is most preferred that the percentage of benzene rings in the polystyrene bearing a functional group be greater than 5%. Even more preferably, this percentage is above 10%.

The preferred supported sequestering agents according to the invention have the following formula:

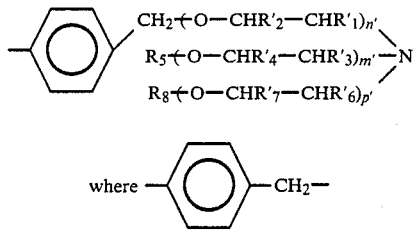

is derived from a chloromethylated or bromomethylated polystyrene cross-linked with divinylbenzene, and having the formula:

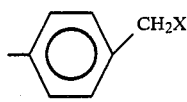

where X denotes Cl or Br.

According to another preferred embodiment of the invention, a macrocyclic polyether or a macrocyclic or dicyclic compound is used, grafted onto a cross-linked organic polymer which comprises a polystyrene obtained by a reaction of suitable amine derivative of the macrocyclic polyether or of the macrocyclic or dicyclic compound with a chloromethylated polystyrene. These preferred supported products have the following formulae:

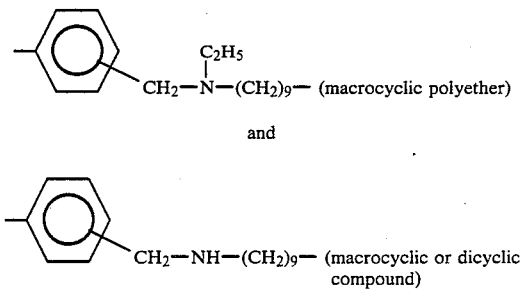

The process of the invention may be carried out in the presence or absence of solvent. In the latter case, the silane starting materials can serve as the solvent. When a solvent is employed, same should meet a number of conditions: it should dissolve starting material silanes; it should also be chemically inert towards the silanes which are introduced or formed.

Preferably, the material selected as solvent is, for example, chlorobenzene, orthodichlorobenzene, benzene, toluene, cyclohexane, heptane, dichloroethane, methylene chloride, dichlorobenzene, tetrahydrofuran, dioxane, and dimethoxyethane.

The selection of the complexing agent or compound most suitable for carrying out the process according to the invention is made, inter alia, by taking into account the size of the cation of the ionic inorganic salt. The larger the size of the cation, the higher the number of oxygen atoms contained in the molecule of the complexing compound must be.

The process according to the invention is advantageously carried out at a temperature ranging from $-30°$ C. to the boiling point of the reaction mixture.

Preferably, the reaction is carried out under atmospheric pressure. Of course, pressures greater or less than atmospheric pressure may also be used.

The complexing compound is used in such amounts that the molar ratio of the complexing compound (or of the active groups of the latter, if the complexing compound is supported) to the ionic inorganic salt preferably ranges from 0.05 to 100. More preferably, this ratio ranges from 0.5 to 5.

The molar ratio of the ionic inorganic salt to the silane starting materials (silane and alkylhydrogenosilane or arylhydrogenosilane) preferably ranges from 10 to 0.0001. It more preferably ranges from 0.5 to 0.001.

The molar ratio of the silane to the alkylhydrogenosilane or arylhydrogenosilane preferably ranges from 0.1 to 5; if this ratio is high, the reaction is limited to the formation of silanes of low hydrogen content, while if this ratio is low, the reaction can be continued up to the formation of silanes of higher hydrogen content and in certain cases up to $SiH_4$.

The molar ratio of the solvent to the silane starting materials advantageously ranges from 0 to 100 and preferably ranges from 0 to 10.

The hydrogenosilane or hydrogenosilanes obtained can be isolated at the rate at which they are formed if they are sparingly soluble in the reaction medium and are sufficiently volatile; the various silanes obtained (the hydrogenosilane or hydrogenosilanes and the alkylsilane or alkylsilanes or arylsilane or arylsilanes formed), as well as the unreacted silanes, can also be separated upon completion of the reaction by techniques which are well known to this art, for example, by distillation, selective dissolution, and the like.

It will be appreciated that the catalyst system employed according to the invention also catalyzes at the same time the dismutation reactions of the silanes containing at least one Si—H bond (as described in French Patent Application No. 8,303,089); thus, the redistribution reaction immediately above described, followed by simultaneous dismutation reactions of the silanes which are present and containing at least one Si—H bond may lead to the production of more or less complex mixtures of silanes. For example, the redistribution reaction may be overall represented as follows:

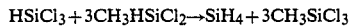

$$HSiCl_3 + 3CH_3HSiCl_2 \rightarrow SiH_4 + 3CH_3SiCl_3$$

and in fact corresponds to the sum of the redistribution reaction

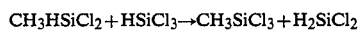

$$CH_3HSiCl_2 + HSiCl_3 \rightarrow CH_3SiCl_3 + H_2SiCl_2$$

and the dismutation reaction $3H_2SiCl_2 \rightarrow SiH_4 + 2HSiCl_3$. In the case were the silane employed for the redistribution reaction is tetrachlorosilane, which does not disproportionate (it does not contain Si—H bonds), if it is desired to avoid the dismutation of the $H_2SiCl_2$ formed by the redistribution reaction, it should be recovered at the same rate as it is being formed.

The grafted complexing compounds employed according to the invention permit the process to preferably be carried out continuously in a column, while the non-grafted complexing compounds permit it to be carried out either continuously or batchwise.

The sequestering agents of the formula (I) used in the process according to the invention can also be prepared as described in published French Patent Application No. 2,450,120.

The present invention thus makes it possible to prepare hydrogenosilanes by a novel redistribution reaction, with an exceptional degree of conversion, and with the use of only small amounts of a catalyst system.

In order to further illustrate the present invention and the advantages thereof, the following specific examples are given, it being understood that same are intended only as illustrative and in nowise limitative.

EXAMPLE 1

The following materials were introduced into an 8 ml flask fitted with a Viton ® dividing membrane:

(i) $19.7 \times 10^{-3}$ moles of chlorobenzene (solvent), namely, 2.219 g;

(ii) $0.54 \times 10^{-3}$ moles of tris-(3,6-dioxaheptyl)-a,mine, namely, 0.173 g (this complexing compound will be designated "TDA 1");

(iii) $0.48 \times 10^{-3}$ moles of LiCl (as the ionic inorganic salt), namely, 20.2 mg.

After having heated the flask to a temperature of 30° C., the following reagents were introduced by means of a syringe:

(iv) $4.05 \times 10^{-3}$ moles of $CH_3SiHCl_2$, namely, 0.466 g, and (v) $5.90 \times 10^{-3}$ moles of $HSiCl_3$, namely, 0.799 g.

The redistribution reaction between the $CH_3SiHCl_2$ and $HSiCl_3$ was followed by periodically analyzing the reaction medium by gas phase chromatography.

After a reaction time of 3 hours, the reaction mixture had the following composition (in percentages by weight):

| | | |
|---|---|---|
| (1) | $SiH_4$ | 0% |
| (2) | $H_3SiCl$ | 0% |
| (3) | $CH_3SiH_2Cl$ | 0% |
| (4) | $H_2SiCl_2$ | 4.12% |
| (5) | $HSiCl_3$ | 15.65% |
| (6) | $CH_3SiHCl_2$ | 8.44% |
| (7) | $SiCl_4$ | 0.68% |
| (8) | $CH_3SiCl_3$ | 5.49% |
| (9) | $C_6H_5Cl$ | 60.34% | which corresponds to a degree of conversion of $HSiCl_3$ of 28% and a degree of conversion of $CH_3SiHCl_2$ of 33%.

EXAMPLE 2

The procedure of Example 1 was repeated, under the same operating conditions, but with an increase in the ratios $$\frac{TDA\ 1 + LiCl}{HSiCl_3 + CH_3SiHCl} \text{ and } \frac{CH_3SiHCl_2}{HSiCl_3}:$$

| | | |
|---|---|---|
| (i) | Chlorobenzene | 10.11 g (89.9 × 10$^{-3}$ moles) |
| (ii) | TDA 1 | 2.019 g (6.24 × 10$^{-3}$ moles) |
| (iii) | LiCl | 0.255 g (6.02 × 10$^{-3}$ moles) |
| (iv) | $HSiCl_3$ | 0.467 g (3.45 × 10$^{-3}$ moles) |
| (v) | $CH_3SiHCl_2$ | 1.644 g (14.3 × 10$^{-3}$ moles) |

After a reaction time of 1 hour 10 minutes, the reaction mixture had the following composition:

| | | |
|---|---|---|
| (1) | $SiH_4$ | 0.09% |
| (2) | $H_3SiCl$ | 0.30% |
| (3) | $CH_3SiH_2Cl$ | 0.22% |
| (4) | $H_2SiCl_2$ | 0.98% |
| (5) | $HSiCl_3$ | 0.93% |
| (6) | $CH_3SiHCl_2$ | 7.62% |
| (7) | $SiCl_4$ | 0% |
| (8) | $CH_3SiCl_3$ | 4.43% |
| (9) | $C_6H_5Cl$ | 69.74% |

This corresponds to a degree of conversion of $HSiCl_3$ of 71% and a degree of conversion of $CH_3SiHCl_2$ of 33%.

It will be appreciated that in this example the increase in the molar ratio $$\frac{CH_3SiHCl_2}{HSiCl_3}$$

made it possible to obtain more highly hydrogenated silanes ($H_3SiCl$ and $SiH_4$) by reaction between the $H_2SiCl_2$ formed and the alkylhydrogenosilane starting material, and also to completely eliminate the formation of $SiCl_4$. These reactions may be accompanied by dismutation reactions of the various silanes present in the reaction medium, these reactions being catalyzed by the catalyst systems of the invention.

The principal reaction, followed by the reactions mentioned immediately above, can thus result in more or less complex mixtures of silanes being obtained.

EXAMPLE 3

The procedure of the preceding examples was repeated, but replacing the $HSiCl_3$ by $SiCl_4$:

| | | |
|---|---|---|
| (i) | Chlorobenzene | 2.262 g (20.1 × 10$^{-3}$ moles) |
| (ii) | TDA 1 | 0.180 g (0.56 × 10$^{-3}$ moles) |
| (iii) | LiCl | 19.6 mg (0.46 × 10$^{-3}$ moles) |
| (iv) | $SiCl_4$ | 0.540 g (3.18 × 10$^{-3}$ moles) |
| (v) | $CH_3SiHCl_2$ | 0.663 g (5.76 × 10$^{-3}$ moles) |

After a reaction time of 25 hours, the reaction mixture had the following composition:

| | | | |
|---|---|---|---|
| (1) | $SiH_4$ | 0% | |
| (2) | $H_3SiCl$ | 0% | |
| (3) | $CH_3SiH_2Cl$ | 0% | |
| (4) | $H_2SiCl_2$ | 0.22% | |
| (5) | $HSiCl_3$ | 6.88% | |
| (6) | $CH_3SiHCl_2$ | 11.74% | |
| (7) | $SiCl_4$ | 5.75% | |
| (8) | $CH_3SiCl_3$ | 8.24% | |
| (9) | $C_6H_5Cl$ | 61.71% | $C_6H_5Cl$ 65.50% |

This corresponds to a degree of conversion of $SiCl_4$ of 61% and a degree of conversion of $CH_3SiHCl_2$ of 35%.

Thermodynamic equilibrium was reached in about 50 hours, when the composition was as follows:

| | | |
|---|---|---|
| (1) | $SiH_4$ | 0.03% |
| (2) | $H_3SiCl$ | 0.18% |
| (3) | $CH_3SiH_2Cl$ | 0.04% |
| (4) | $H_2SiCl_2$ | 2.42% |
| (5) | $HSiCl_3$ | 7.76% |
| (6) | $CH_3SiHCl_2$ | 4.39% |
| (7) | $SiCl_4$ | 0.28% |
| (8) | $CH_3SiCl_3$ | 17.70% |

-continued

| | | |
|---|---|---|
| (9) C₆H₅Cl | 61.71% | |

This corresponds to a degree of conversion of $SiCl_4$ of 98% and a degree of conversion of $CH_3SiHCl_2$ of 76%.

EXAMPLE 4

The procedure of Example 3 was repeated, except that the LiCl salt was replaced by LiBr:

| | | |
|---|---|---|
| (i) Chlorobenzene | 2.248 g (20.0 × 10⁻³ moles) | |
| (ii) TDA 1 | 0.270 g (0.84 × 10⁻³ moles) | |
| (iii) LiBr | 39.7 mg (0.46 × 10⁻³ moles) | |
| (iv) SiCl₄ | 0.488 g (2.87 × 10⁻³ moles) | |
| (v) CH₃SiHCl₂ | 0.686 g (5.96 × 10⁻³ moles) | |

After a reaction time of 6 hours, the reaction mixture had the following composition:

| | | |
|---|---|---|
| (1) SiH₄ | 0% | |
| (2) H₃SiCl | 0% | |
| (3) CH₃SiH₂Cl | 0.02% | |
| (4) H₂SiCl₂ | 0.05% | |
| (5) HSiCl₃ | 3.38% | |
| (6) CH₃SiHCl₂ | 15.32% | |
| (7) SiCl₄ | 8.74% | |
| (8) CH₃SiCl₃ | 3.93% | |
| (9) C₆H₅Cl | 60.24% | |

This corresponds to a degree of conversion of $SiCl_4$ of 33% and a degree of conversion of $CH_3SiHCl_2$ of 17%.

Thermodynamic equilibrium was reached in about 22 hours, the composition then being as follows:

| | | |
|---|---|---|
| (1) SiH₄ | 0.03% | |
| (2) H₃SiCl | 0.25% | |
| (3) CH₃SiH₂Cl | 0.06% | |
| (4) H₂SiCl₂ | 2.84% | |
| (5) HSiCl₃ | 5.74% | |
| (6) CH₃SiHCl₂ | 5.06% | |
| (7) SiCl₄ | 0.27% | |
| (8) CH₃SiCl₃ | 17.19% | |
| (9) C₆H₅Cl | 60.24% | |

This corresponds to a degree of conversion of $SiCl_4$ of 98% and a degree of conversion of $CH_3SiHCl_2$ of 72%.

EXAMPLE 5

The procedure of the preceding examples was repeated, using $CH_3SiHCl_2$ and $H_2SiCl_2$ reagents, under the same operating conditions:

| | | |
|---|---|---|
| (i) Chlorobenzene | 2.264 g (20.1 × 10⁻³ moles) | |
| (ii) TDA 1 | 0.185 g (0.57 × 10⁻³ moles) | |
| (iii) LiCl | 22.5 mg (0.53 × 10⁻³ moles) | |
| (iv) H₂SiCl₂ | 0.537 g (5.32 × 10⁻³ moles) | |
| (v) CH₃SiHCl₂ | 0.535 g (4.65 × 10⁻³ moles) | |

After a reaction time of 3 hours, the reaction mixture had the following composition:

| | | |
|---|---|---|
| (1) SiH₄ | 0.73% | |
| (2) H₃SiCl | 2.37% | |
| (3) CH₃SiH₂Cl | 0.23% | |
| (4) H₂SiCl₂ | 5.99% | |
| (5) HSiCl₃ | 4.40% | |
| (6) CH₃SiHCl₂ | 8.96% | |
| (7) SiCl₄ | 0.04% | |
| (8) CH₃SiCl₃ | 7.55% | |
| (9) C₆H₅Cl | 63.90% | |

This corresponds to a degree of conversion of $H_2SiCl_2$ of 61% and a degree of conversion of $CH_3SiHCl_2$ of 41%.

In this experiment, the reaction between the $H_2SiCl_2$ and $CH_3SiHCl_2$ was accompanied by the dismutation of $H_2SiCl_2$.

EXAMPLE 6

In this example, the procedure of Example 1 was repeated, but with the catalyst system TDA 1+LiCl being replaced by the system TDA 1+LiBr:

| | | |
|---|---|---|
| (i) Chlorobenzene | 2.475 g (22.0 × 10⁻³ moles) | |
| (ii) TDA 1 | 0.210 g (0.65 × 10⁻³ moles) | |
| (iii) LiBr | 41.0 mg (0.47 × 10⁻³ moles) | |
| (iv) HSiCl₃ | 0.704 g (5.20 × 10⁻³ moles) | |
| (v) CH₃SiHCl₂ | 0.909 g (7.90 × 10⁻³ moles) | |

After a reaction time of 5 hours, the reaction mixture had the following composition:

| | | |
|---|---|---|
| (1) SiH₄ | 0.06% | |
| (2) H₃SiCl | 0.12% | |
| (3) CH₃SiH₂Cl | 0.13% | |
| (4) H₂SiCl₂ | 4.00% | |
| (5) HSiCl₃ | 10.11% | |
| (6) CH₃SiHCl₂ | 15.16% | |
| (7) SiCl₄ | 0.31% | |
| (8) CH₃SiCl₃ | 7.27% | |
| (9) C₆H₅Cl | 57.04% | |

This corresponds to a degree of conversion of $HSiCl_3$ of 38% and a degree of conversion of $CH_3SiHCl_2$ of 28%.

EXAMPLE 7

The procedure of the preceding examples was repeated, using the catalyst system TDA 1+LiF, again in the presence of $C_6H_5Cl$ as the solvent:

| | | |
|---|---|---|
| (i) Chlorobenzene | 3.092 g (27.5 × 10⁻³ moles) | |
| (ii) TDA 1 | 0.167 g (0.52 × 10⁻³ moles) | |
| (iii) LiF | 13.7 mg (0.53 × 10⁻³ moles) | |
| (iv) HSiCl₃ | 0.538 g 3.97 × 10⁻³ moles) | |
| (v) CH₃SiHCl₂ | 0.910 g (7.91 × 10⁻³ moles) | |

After a reaction time of 5 hours, the reaction mixture had the following composition:

| | | |
|---|---|---|
| (1) SiH₄ | 0.05% | |
| (2) H₃SiCl | 0.10% | |
| (3) CH₃SiH₂Cl | 0.15% | |
| (4) H₂SiCl₂ | 3.42% | |
| (5) HSiCl₃ | 6.28% | |
| (6) CH₃SiHCl₂ | 14.18% | |
| (7) SiCl₄ | 0.14% | |
| (8) CH₃SiCl₃ | 6.33% | |
| (9) C₆H₅Cl | 65.50% | |

This corresponds to a degree of conversion of $HSiCl_3$ of 45% and a degree of conversion of $CH_3SiHCl_2$ of 26%.

After a reaction time of 24 hours (when equilibrium had been reached), the mixture had the following composition:

| | | |
|---|---|---|
| (1) | $SiH_4$ | 0.34% |
| (2) | $H_3SiCl$ | 0.99% |
| (3) | $CH_3SiH_2Cl$ | 0.24% |
| (4) | $H_2SiCl_2$ | 3.53% |
| (5) | $HSiCl_3$ | 3.19% |
| (6) | $CH_3SiHCl_2$ | 7.53% |
| (7) | $SiCl_4$ | 0.04% |
| (8) | $CH_3SiCl_3$ | 14.82% |
| (9) | $C_6H_5Cl$ | 65.50% |

This corresponds to a degree of conversion of $HSiCl_3$ of 72% and a degree of conversion of $CH_3SiHCl_2$ of 61%.

EXAMPLE 8

The procedure of the preceding examples was again repeated, but using the catalyst system TDA 1+NaI:

| | | |
|---|---|---|
| (i) | Chlorobenzene | 1.775 g (15.8 × $10^{-3}$ moles) |
| (ii) | TDA 1 | 1.156 g (3.57 × $10^{-3}$ moles) |
| (iii) | NaI | 0.188 g (1.25 × $10^{-3}$ moles) |
| (iv) | $HSiCl_3$ | 0.480 g (3.54 × $10^{-3}$ moles) |
| (v) | $CH_3SiHCl_2$ | 1.153 g (10.0 × $10^{-3}$ moles) |

After a reaction time of 24 hours, the reaction mixture had the following composition:

| | | |
|---|---|---|
| (1) | $SiH_4$ | 0.16% |
| (2) | $H_3SiCl$ | 0.47% |
| (3) | $CH_3SiH_2Cl$ | 0.38% |
| (4) | $H_2SiCl_2$ | 4.57% |
| (5) | $HSiCl_3$ | 6.28% |
| (6) | $CH_3SiHCl_2$ | 24.25% |
| (7) | $SiCl_4$ | 0.05% |
| (8) | $CH_3SiCl_3$ | 11.76% |
| (9) | $C_6H_5Cl$ | 52.08% |

This corresponds to a degree of conversion of $HSiCl_3$ of 55% and a degree of conversion of $CH_3SiHCl_2$ of 27%.

EXAMPLE 9

The procedure of the proceding examples were again repeated, but using the catalyst system TDA 1×$NH_4Cl$:

| | | |
|---|---|---|
| (i) | Chlorobenzene | 2.146 g (19.1 × $10^{-3}$ moles) |
| (ii) | TDA 1 | 1.154 g (3.60 × $10^{-3}$ moles) |
| (iii) | $NH_4Cl$ | 66 mg (1.22 × $10^{-3}$ moles) |
| (iv) | $HSiCl_3$ | 0.767 g (5.66 × $10^{-3}$ moles) |
| (v) | $CH_3SiHCl_2$ | 1.085 g (9.43 × $10^{-3}$ moles) |

After a reaction time of 4 hours, the reaction mixture had the following composition:

| | | |
|---|---|---|
| (1) | $SiH_4$ | 0.33% |
| (2) | $H_3SiCl$ | 1.05% |
| (3) | $CH_3SiH_2Cl$ | 0.24% |
| (4) | $H_2SiCl_2$ | 7.00% |
| (5) | $HSiCl_3$ | 6.17% |
| (6) | $CH_3SiHCl_2$ | 11.39% |
| (7) | $SiCl_4$ | 0.12% |
| (8) | $CH_3SiCl_3$ | 20.01% |
| (9) | $C_6H_5Cl$ | 53.69% |

This corresponds to a degree of conversion of $HSiCl_3$ of 68% and a degree of conversion of $CH_3SiHCl_2$ of 58%.

EXAMPLE 10

The procedure of Example 7 was repeated, using a catalyst mixture of TDA 1×LiF, but using toluene as the solvent, in place of chlorobenzene:

| | | |
|---|---|---|
| (i) | Toluene | 2.369 g (25.7 × $10^{-3}$ moles) |
| (ii) | TDA 1 | 0.169 g (0.52 × $10^{-3}$ moles) |
| (iii) | LiF | 13.0 mg (0.50 × $10^{-3}$ moles) |
| (iv) | $HSiCl_3$ | 0.524 g (3.87 × $10^{-3}$ moles) |
| (v) | $CH_3SiHCl_2$ | 0.782 g (6.80 × $10^{-3}$ moles) |

After a reaction time of 10 hours, the reaction mixture had the following composition:

| | | |
|---|---|---|
| (1) | $SiH_4$ | 0.02% |
| (2) | $H_3SiCl$ | 0.07% |
| (3) | $CH_3SiHCl_2$ | 0.13% |
| (4) | $H_2SiCl_2$ | 3.40% |
| (5) | $HSiCl_3$ | 8.53% |
| (6) | $CH_3SiHCl_2$ | 15.74% |
| (7) | $SiCl_4$ | 0.31% |
| (8) | $CH_3SiCl_3$ | 5.66% |
| (9) | $C_6H_5CH_3$ | 61.41% |

This corresponds to a degree of conversion of $HSiCl_3$ of 37% and a degree of conversion of $CH_3SiHCl_2$ of 22%.

EXAMPLE 11

The procedure of the preceding examples was repeated, using the catalyst mixture TDA 1+LiBr, again in the presence of toluene as the solvent:

| | | |
|---|---|---|
| (i) | Toluene | 1.184 g (12.8 × $10^{-3}$ moles) |
| (ii) | TDA 1 | 1.058 g (3.27 × $10^{-3}$ moles) |
| (iii) | LiBr | 94.8 mg (1.09 × $10^{-3}$ moles) |
| (iv) | $HSiCl_3$ | 0.654 g (4.83 × $10^{-3}$ moles) |
| (v) | $CH_3SiHCl_2$ | 1.520 g (9.70 × $10^{-3}$ moles) |

After a reaction time of 5 hours, the reaction mixture had the following composition:

| | | |
|---|---|---|
| (1) | $SiH_4$ | 0.16% |
| (2) | $H_3SiCl$ | 1.08% |
| (3) | $CH_3SiH_2Cl$ | 0.14% |
| (4) | $H_2SiCl_2$ | 6.16% |
| (5) | $HSiCl_3$ | 11.00% |
| (6) | $CH_3SiHCl_2$ | 24.88% |
| (7) | $SiCl_4$ | 0% |
| (8) | $CH_3SiCl_3$ | 16.50% |
| (9) | $C_6H_5CH_3$ | 40.08% |

This corresponds to a degree of conversion of $HSiCl_3$ of 50% and a degree of conversion of $CH_3SiHCl_2$ of 25%.

EXAMPLE 12

The procedure of the preceding example was repeated, but using heptane as the solvent:

| (i) Heptane | 1.340 g (13.5 × 10⁻³ moles) |
|---|---|
| (ii) TDA 1 | 1.147 g (3.54 × 10⁻³ moles) |
| (iii) LiBr | 0.103 g (1.14 × 10⁻³ moles) |
| (iv) HSiCl$_3$ | 0.765 g (5.65 × 10⁻³ moles) |
| (v) CH$_3$SiHCl$_2$ | 1.224 g (7.81 × 10⁻³ moles) |

After a reaction time of 27 hours, the reaction mixture had the following composition:

| (1) SiH$_4$ | 0.27% |
|---|---|
| (2) H$_3$SiCl | 1.11% |
| (3) CH$_3$SiH$_2$Cl | 0.32% |
| (4) H$_2$SiCl$_2$ | 6.87% |
| (5) HSiCl$_3$ | 12.77% |
| (6) CH$_3$SiHCl$_2$ | 14.43% |
| (7) SiCl$_4$ | 0.06% |
| (8) CH$_3$SiCl$_3$ | 19.41% |
| (9) C$_7$H$_{16}$ | 44.76% |

This corresponds to a degree of conversion of HSiCl$_3$ of 50% and a degree of conversion of CH$_3$SiHCl$_2$ of 52%.

EXAMPLE 13

The procedure of the preceding examples was repeated, except that dioxane was used as the solvent:

| (i) Dioxane | 1.350 g (15.3 × 10⁻³ moles) |
|---|---|
| (ii) TDA 1 | 1.134 g (3.51 × 10⁻³ moles) |
| (iii) LiBr | 0.102 g (1.17 × 10⁻³ moles) |
| (iv) HSiCl$_3$ | 0.597 g (4.41 × 10⁻³ moles) |
| (v) CH$_3$SiHCl$_2$ | 1.352 g (8.63 × 10⁻³ moles) |

After a reaction time of 2 hours, the reaction mixture had the following composition:

| (1) SiH$_4$ | 0.04% |
|---|---|
| (2) H$_3$SiCl | 0.32% |
| (3) CH$_3$SiH$_2$Cl | 0.08% |
| (4) H$_2$SiCl$_2$ | 2.31% |
| (5) HSiCl$_3$ | 15.83% |
| (6) CH$_3$SiHCl$_2$ | 29.78% |
| (7) SiCl$_4$ | 0.58% |
| (8) CH$_3$SiCl$_3$ | 5.09% |
| (9) C$_4$H$_8$O$_2$ | 45.97% |

This corresponds to a degree of conversion of HSiCl$_3$ of 22% and a degree of conversion of CH$_3$SiHCl$_2$ of 12%.

EXAMPLE 14

In this example, a redistribution reaction between HSiCl$_3$ and CH$_3$SiHCl$_2$ is illustrated, again in the presence of TDA 1+LiBr, but without a solvent:

| (i) TDA 1 | 0.327 g (1.01 × 10⁻³ moles) |
|---|---|
| (ii) LiBr | 77.0 mg (0.86 × 10⁻³ moles) |
| (iii) HSiCl$_3$ | 0.867 g (6.40 × 10⁻³ moles) |
| (iv) CH$_3$SiHCl$_2$ | 1.791 g (15.6 × 10⁻³ moles) |

After a reaction time of 4 hours, the reaction mixture had the following composition:

| (1) SiH$_4$ | 0.39% |
|---|---|
| (2) H$_3$SiCl | 1.09% |
| (3) CH$_3$SiH$_2$Cl | 0.63% |
| (4) H$_2$SiCl$_2$ | 9.93% |
| (5) HSiCl$_3$ | 10.88% |
| (6) CH$_3$SiHCl$_2$ | 37.68% |
| (7) SiCl$_4$ | 0.33% |
| (8) CH$_3$SiCl$_3$ | 25.87% |

This corresponds to a degree of conversion of HSiCl$_3$ of 62% and a degree of conversion of CH$_3$SiHCl$_2$ of 38%.

EXAMPLE 15

The procedure of the preceding examples was repeated, for the reaction between HSiCl$_3$ and CH$_3$SiHCl$_2$, in the presence of tris-(3,6-dioxaoctyl)-amine (TDA 2) and LiBr as the catalyst system and using chlorobenzene as the solvent:

| (i) Chlorobenzene | 1.931 g (17.2 × 10⁻³ moles) |
|---|---|
| (ii) TDA 2 | 1.303 g (3.57 × 10⁻³ moles) |
| (iii) LiBr | 0.116 g (1.33 × 10⁻³ moles) |
| (iv) HSiCl$_3$ | 0.748 g (5.52 × 10⁻³ moles) |
| (v) CH$_3$SiHCl$_2$ | 1.326 g (11.5 × 10⁻³ moles) |

After a reaction time of 1 hour 30 minutes, the reaction mixture had the following composition:

| (1) SiH$_4$ | 0.28% |
|---|---|
| (2) H$_3$SiCl | 1.16% |
| (3) CH$_3$SiH$_2$Cl | 0.38% |
| (4) H$_2$SiCl$_2$ | 6.63% |
| (5) HSiCl$_3$ | 6.19% |
| (6) CH$_3$SiHCl$_2$ | 17.52% |
| (7) SiCl$_4$ | 0.08% |
| (8) CH$_3$SiCl$_3$ | 19.56% |
| (9) C$_6$H$_5$Cl | 48.20% |

This corresponds to a degree of conversion of HSiCl$_3$ of 67% and a degree of conversion of CH$_3$SiHCl$_2$ of 47%.

EXAMPLE 16

The procedure of the preceding example was repeated, except using tris-(3,6-dioxadecyl)-amine (TDA 4) as the complexing agent:

| (i) Chlorobenzene | 2.054 g (18.3 × 10⁻³ moles) |
|---|---|
| (ii) TDA 4 | 1.673 g (3.73 × 10⁻³ moles) |
| (iii) LiBr | 98.8 mg (1.14 × 10⁻³ moles) |
| (iv) HSiCl$_3$ | 0.665 g (4.91 × 10⁻³ moles) |
| (v) CH$_3$SiHCl$_2$ | 1.271 g (11.1 × 10⁻³ moles) |

After a reaction time of 1 hour 40 minutes, the reaction mixture had the following composition:

| (1) SiH$_4$ | 0.20% |
|---|---|
| (2) H$_3$SiCl | 0.70% |
| (3) CH$_3$SiH$_2$Cl | 0.34% |
| (4) H$_2$SiCl$_2$ | 5.11% |
| (5) HSiCl$_3$ | 7.43% |
| (6) CH$_3$SiHCl$_2$ | 20.56% |
| (7) SiCl$_4$ | 0.13% |
| (8) CH$_3$SiCl$_3$ | 14.05% |
| (9) C$_6$H$_5$Cl | 51.48% |

This corresponds to a degree of conversion of HSiCl$_3$ of 55% and a degree of conversion of CH$_3$SiHCl$_2$ of 35%.

EXAMPLE 17

The procedure of the preceding examples was repeated, using tris-(3,6,9-trioxadecyl)-amine (TTA) as the complexing agent and KCl as the ionic salt:

| | | |
|---|---|---|
| (i) | Chlorobenzene | 2.303 g (20.5 × 10⁻³ moles) |
| (ii) | TTA 1 | 1.591 g (3.50 × 10⁻³ moles) |
| (iii) | KCl | 0.100 g (1.34 × 10⁻³ moles) |
| (iv) | HSiCl₃ | 0.662 g (4.88 × 10⁻³ moles) |
| (v) | CH₃SiHCl₂ | 1.376 g (12.0 × 10⁻³ moles) |

After a reaction time of 2 hours 30 minutes, the reaction mixture had the following composition:

| | | |
|---|---|---|
| (1) | $SiH_4$ | 0.09% |
| (2) | $H_3SiCl$ | 0.46% |
| (3) | $CH_3SiH_2Cl$ | 0.24% |
| (4) | $H_2SiCl_2$ | 5.33% |
| (5) | $HSiCl_3$ | 6.52% |
| (6) | $CH_3SiHCl_2$ | 22.61% |
| (7) | $SiCl_4$ | 0.31% |
| (8) | $CH_3SiCl_3$ | 11.37% |
| (9) | $C_6H_5Cl$ | 53.07% |

This corresponds to a degree of conversion of $HSiCl_3$ of 57% and a degree of conversion of $CH_3SiHCl_2$ of 29%.

EXAMPLE 18

The procedure of the preceding examples was repeated, using tris-(3,6,9-trioxaundecyl)-amine (TTA 2)+KCl as the catalyst mixture:

The experiment was comparable to that of the preceding example, except that the complexing agent had again been changed:

| | | |
|---|---|---|
| (i) | Chlorobenzene | 2.114 g (18.8 × 10⁻³ moles) |
| (ii) | TTA 2 | 1.801 g (3.62 × 10⁻³ moles) |
| (iii) | KCl | 97 mg (1.30 × 10⁻³ moles) |
| (iv) | HSiCl₃ | 0.603 g (4.45 × 10⁻³ moles) |
| (v) | CH₃SiHCl₂ | 1.519 g (13.2 × 10⁻³ moles) |

After a reaction time of 2 hours 40 minutes, the reaction mixture had the following composition:

| | | |
|---|---|---|
| (1) | $SiH_4$ | 0.36% |
| (2) | $H_3SiCl$ | 0.80% |
| (3) | $CH_3SiH_2Cl$ | 0.67% |
| (4) | $H_3SiCl_2$ | 4.03% |
| (5) | $HSiCl_3$ | 5.63% |
| (6) | $CH_3SiHCl_2$ | 22.81% |
| (7) | $SiCl_4$ | 0.08% |
| (8) | $CH_3SiCl_3$ | 15.71% |
| (9) | $C_6H_5Cl$ | 49.91% |

This corresponds to a degree of conversion of $HSiCl_3$ of 60% and a degree of conversion of $CH_3SiHCl_2$ of 36%.

EXAMPLE 19

The procedure of the preceding examples was repeated, for redistribution between $CH_3SiHCl_2$ and $HSiCl_3$ in the presence of tris-(3,6,9-trioxaundecyl)-amine (TTA 2), grafted onto a polystyrene resin:

| | | |
|---|---|---|
| (i) | Chlorobenzene | 5.242 g (46.6 × 10⁻³ moles) |
| (ii) | Grafted TTA 2 | 1.897 g (3.39 × 10⁻³ moles) |
| (iii) | LiCl | 54.4 mg (1.28 × 10⁻³ moles) |
| (iv) | HSiCl₃ | 0.649 m (4.78 × 10⁻³ moles) |
| (v) | CH₃SiHCl₂ | 1.544 g (13.4 × 10⁻³ moles) |

After a reaction time of 52 hours, the reaction mixture had the following composition:

| | | |
|---|---|---|
| (1) | $SiH_4$ | 0% |
| (2) | $H_3SiCl$ | 0% |
| (3) | $CH_3SiH_2Cl$ | 0% |
| (4) | $H_2SiCl_2$ | 1.26% |
| (5) | $HSiCl_3$ | 6.99% |
| (6) | $CH_3SiHCl_2$ | 19.59% |
| (7) | $SiCl_4$ | 0.50% |
| (8) | $CH_3SiCl_3$ | 1.42% |
| (9) | $C_6H_5Cl$ | 70.24% |

This corresponds to a degree of conversion of $HSiCl_3$ of 19% and a degree of conversion of $CH_3SiHCl_2$ of 5%.

EXAMPLE 20

The procedure of the preceding example was repeated, except that the grafted catalyst was changed, tris-(3,6-dioxaheptyl)-amine (TDA 1) being used in place of TTA 2, and the salt was also changed, LiBr being used in place of LiCl:

| | | |
|---|---|---|
| (i) | Chlorobenzene | 3.993 g (35.5 × 10⁻³ moles) |
| (ii) | Grafted TDA 1 | 1.095 g (2.75 × 10⁻³ moles) |
| (iii) | LiBr | 51.9 mg (0.63 × 10⁻³ moles) |
| (iv) | HSiCl₃ | 0.834 g (6.15 × 10⁻³ moles) |
| (v) | CH₃SiHCl₂ | 1.398 g (12.1 × 10⁻³ moles) |

After a reaction time of 24 hours, the reaction mixture had the following composition:

| | | |
|---|---|---|
| (1) | $SiH_4$ | 0.15% |
| (2) | $H_3SiCl$ | 0.43% |
| (3) | $CH_3SiH_2Cl$ | 0.22% |
| (4) | $H_2SiCl_2$ | 5.66% |
| (5) | $HSiCl_3$ | 4.53% |
| (6) | $CH_3SiHCl_2$ | 12.19% |
| (7) | $SiCl_4$ | 0.03% |
| (8) | $CH_3SiCl_3$ | 12.83% |
| (9) | $C_6H_5Cl$ | 63.95% |

This corresponds to a degree of conversion of $HSiCl_3$ of 66% and a degree of conversion of $CH_3SiHCl_2$ of 46%.

EXAMPLE 21

The procedure of the preceding examples was repeated, but reacting $HSiCl_3$ with $CH_3SiHCl_2$ in the presence of KCl and 4,7,13,16,21,24-hexaoxa-1,10-diazabicyclo-8,8,8-hexacosane (commercially available under the trademark Kryptofix 2,2,2 ®), and carried out in a chlorobenzene solvent medium:

| | | |
|---|---|---|
| (i) | Chlorobenzene | 2.973 g (26.4 × 10⁻³ moles) |
| (ii) | Kryptofix 2,2,2 | 0.175 g (0.46 × 10⁻³ moles) |
| (iii) | KCl | 41.4 mg (0.56 × 10⁻³ moles) |
| (iv) | HSiCl₃ | 0.637 g (4.70 × 10⁻³ moles) |
| (v) | CH₃SiHCl₂ | 0.966 g (8.40 × 10⁻³ moles) |

After a reaction time of 4 hours, the reaction mixture had the following composition:

| | | |
|---|---|---|
| (1) | SiH$_4$ | 0.06% |
| (2) | H$_3$SiCl | 0.39% |
| (3) | CH$_3$SiH$_2$Cl | 0.12% |
| (4) | H$_2$SiCl$_2$ | 4.30% |
| (5) | HSiCl$_3$ | 6.19% |
| (6) | CH$_3$SiHCl$_2$ | 13.18% |
| (7) | SiCl$_4$ | 0.35% |
| (8) | CH$_3$SiCl$_3$ | 8.86% |
| (9) | C$_6$H$_5$Cl | 62.04% |

This corresponds to a degree of conversion of HSiCl$_3$ of 53% and a degree of conversion of CH$_3$SiHCl$_2$ of 35%.

EXAMPLE 22

The procedure of the preceding example was repeated, except that the Kryptofix 2,2,2 was replaced by 1,4,7,10,13,16-hexaoxacyclooctadecane, marketed under the trademark 18 Crown 6 ®:

| | | |
|---|---|---|
| (i) | Chlorobenzene | 3.116 g (27.7 × 10$^{-3}$ moles) |
| (ii) | 18 Crown 6 | 0.160 g (0.61 × 10$^{-3}$ moles) |
| (iii) | KCl | 50.1 mg (0.67 × 10$^{-3}$ moles) |
| (iv) | HSiCl$_3$ | 0.532 g (3.93 × 10$^{-3}$ moles) |
| (v) | CH$_3$SiHCl$_2$ | 0.985 g (8.56 × 10$^{-3}$ moles) |

After a reaction time of 100 hours, the reaction mixture had the following composition:

| | | |
|---|---|---|
| (1) | SiH$_4$ | 0.05% |
| (2) | H$_3$SiCl | 0.16% |
| (3) | CH$_3$SiH$_2$Cl | 0.17% |
| (4) | H$_2$SiCl$_2$ | 3.09% |
| (5) | HSiCl$_3$ | 6.24% |
| (6) | CH$_3$SiHCl$_2$ | 15.34% |
| (7) | SiCl$_4$ | 0.11% |
| (8) | CH$_3$SiCl$_3$ | 6.17% |
| (9) | C$_6$H$_5$Cl | 64.34% |

This corresponds to a degree of conversion of HSiCl$_3$ of 43% and a degree of conversion of CH$_3$SiHCl$_2$ of 25%.

EXAMPLE 23

The procedure of the preceding examples was repeated for reaction between HSiCl$_3$ and (CH$_3$)$_2$SiHCl in the presence of the catalyst system TDA 1+LiCl, and using C$_6$H$_5$Cl as the solvent:

| | | |
|---|---|---|
| (i) | Chlorobenzene | 1.743 g (15.5 × 10$^{-3}$ moles) |
| (ii) | TDA 1 | 0.167 g (0.52 × 10$^{-3}$ moles) |
| (iii) | LiCl | 18.9 mg (0.45 × 10$^{-3}$ moles) |
| (iv) | HSiCl$_3$ | 0.826 g (6.10 × 10$^{-3}$ moles) |
| (v) | (CH$_3$)$_2$SiHCl | 0.295 g (3.12 × 10$^{-3}$ moles) |

After a reaction time of 43 hours, the reaction mixture had the following composition:

| | | |
|---|---|---|
| (1) | SiH$_4$ | 0% |
| (2) | H$_3$SiCl | 0% |
| (3) | H$_2$SiCl$_2$ | 5.03% |
| (4) | HSiCl$_3$ | 19.72% |
| (5) | (CH$_3$)$_2$SiHCl | 5.84% |
| (6) | SiCl$_4$ | 0.80% |
| (7) | (CH$_3$)$_2$SiCl$_2$ | 5.84% |
| (8) | C$_6$H$_5$Cl | 57.14% |

This corresponds to a degree of conversion of HSiCl$_3$ of 27% and a degree of conversion of (CH$_3$)$_2$SiHCl of 44%.

Thermodynamic equilibrium was reached in about 300 hours, at which stage the reaction mixture had the following composition.

| | | |
|---|---|---|
| (1) | SiH$_4$ | 0.13% |
| (2) | H$_3$SiCl | 0.76% |
| (3) | H$_2$SiCl$_2$ | 6.56% |
| (4) | HSiCl$_3$ | 15.98% |
| (5) | (CH$_3$)$_2$SiHCl | 0.40% |
| (6) | SiCl$_4$ | 0.28% |
| (7) | (CH$_3$)$_2$SiCl$_2$ | 12.65% |
| (8) | C$_6$H$_5$Cl | 57.14% |

This corresponds to a degree of conversion of HSiCl$_3$ of 41% and a degree of conversion of (CH$_3$)$_2$SiHCl of 96%.

EXAMPLE 24

The procedure of the preceding examples was repeated, for redistribution reaction between SiCl$_4$ and (CH$_3$CH$_2$)$_3$SiH in the presence of TDA 1+LiBr as the catalyst system, again using chlorobenzene as the solvent:

| | | |
|---|---|---|
| (i) | Chlorobenzene | 2.044 g (18.2 × 10$^{-3}$ moles) |
| (ii) | TDA 1 | 1.901 g (5.87 × 10$^{-3}$ moles) |
| (iii) | LiBr | 0.170 g (1.96 × 10$^{-3}$ moles) |
| (iv) | SiCl$_4$ | 1.068 g (6.28 × 10$^{-3}$ moles) |
| (v) | (CH$_3$CH$_2$)$_3$SiH | 1.012 g (8.72 × 10$^{-3}$ moles) |

After a reaction time of 20 hours, the reaction mixture had the following composition:

| | | |
|---|---|---|
| (1) | HSiCl$_3$ | 13.92% |
| (2) | SiCl$_4$ | 8.40% |
| (3) | (CH$_3$CH$_2$)$_3$SiH | 12.63% |
| (4) | (CH$_3$CH$_2$)$_3$SiCl | 15.49% |
| (5) | C$_6$H$_5$Cl | 49.56% |

This corresponds to a degree of conversion of SiCl$_4$ of 68%.

EXAMPLE 25

The procedure of the preceding examples was repeated, for redistribution reaction between HSiCl$_3$ and (C$_6$H$_5$)$_2$SiHCl:

| | | |
|---|---|---|
| (i) | Chlorobenzene | 1.834 g (16.3 × 10$^{-3}$ moles) |
| (ii) | TDA 1 | 1.490 g (4.60 × 10$^{-3}$ moles) |
| (iii) | LiBr | 0.134 g (1.54 × 10$^{-3}$ moles) |
| (iv) | HSiCl$_3$ | 0.601 g (4.44 × 10$^{-3}$ moles) |
| (v) | (C$_6$H$_5$)$_2$SiHCl | 3.086 g (14.1 × 10$^{-3}$ moles) |

After a reaction time of 23 hours, the reaction mixture had the following composition:

| | | |
|---|---|---|
| (1) | SiH$_4$ | 1.25% |
| (2) | H$_3$SiCl | 1.33% |
| (3) | H$_2$SiCl$_2$ | 1.32% |
| (4) | HSiCl$_3$ | 1.10% |
| (5) | SiCl$_4$ | 0.06% |
| (6) | (C$_6$H$_5$)$_2$SiHCl | 18.89% |
| (7) | (C$_6$H$_5$)$_2$SiCl$_2$ | 42.85% |
| (8) | C$_6$H$_5$Cl | 33.20% |

This corresponds to a degree of conversion of $HSiCl_3$ of 90% and a degree of conversion of $(C_6H_5)_2SiHCl$ of 66%.

EXAMPLE 26

The procedure of the preceding example was repeated, but replacing $(C_6H_5)_2SiHCl$ by $C_6H_5(CH_3)SiHCl$:

| | | |
|---|---|---|
| (i) Chlorobenzene | 1.760 g (15.6 × $10^{-3}$ moles) | |
| (ii) TDA 1 | 1.289 g (3.98 × $10^{-3}$ moles) | |
| (iii) LiBr | 0.116 g (1.33 × $10^{-3}$ moles) | |
| (iv) $HSiCl_3$ | 0.569 g (4.19 × $10^{-3}$ moles) | |
| (v) $C_6H_5(CH_3)SiHCl$ | 1.305 g (8.34 × $10^{-3}$ moles) | |

After a reaction time of 7 hours, the reaction mixture had the following composition:

| | | |
|---|---|---|
| (1) $SiH_4$ | 0.26% | |
| (2) $H_3SiCl$ | 1.43% | |
| (3) $H_2SiCl_2$ | 3.56% | |
| (4) $HSiCl_3$ | 6.78% | |
| (5) $SiCl_4$ | 0.05% | |
| (6) $C_6H_5(CH_3)SiHCl$ | 19.87% | |
| (7) $C_6H_5(CH_3)SiCl_2$ | 19.62% | |
| (8) $C_6H_5Cl$ | 48.43% | |

This corresponds to a degree of conversion of $HSiCl_3$ of 57% and a degree of conversion of $C_6H_5(CH_3)SiHCl$ of 45%.

EXAMPLE 27

The procedure of the preceding example was repeated, but the reaction was carried out in the absence of a solvent:

| | | |
|---|---|---|
| (i) TDA 1 | 1.005 g (3.11 × $10^{-3}$ moles) | |
| (ii) LiBr | 90.1 g (1.03 × $10^{-3}$ moles) | |
| (iii) $HSiCl_3$ | 0.639 g (4.72 × $10^{-3}$ moles) | |
| (iv) $C_6H_5(CH_3)SiHCl$ | 0.993 g (6.34 × $10^{-3}$ moles) | |

After a reaction time of 7 hours, the reaction mixture had the following composition:

| | | |
|---|---|---|
| (1) $SiH_4$ | 0.84% | |
| (2) $H_3SiCl$ | 3.99% | |
| (3) $H_2SiCl_2$ | 10.52% | |
| (4) $HSiCl_3$ | 13.36% | |
| (5) $SiCl_4$ | 0% | |
| (6) $C_6H_5(CH_3)SiHCl$ | 13.34% | |
| (7) $C_6H_5(CH_3)SiCl_2$ | 57.95% | |

This corresponds to a degree of conversion of $HSiCl_3$ of 66% and a degree of conversion of $C_6H_5(CH_3)SiHCl$ of 78%.

EXAMPLE 28

The procedure of the preceding example (without a solvent) was repeated, for redistribution reaction between $SiCl_4$ and $C_6H_5(CH_3)SiH_2$:

| | | |
|---|---|---|
| (i) TDA 1 | 1.583 g (4.90 × $10^{-3}$ moles) | |
| (ii) LiBr | 0.142 g (1.63 × $10^{-3}$ moles) | |
| (iii) $SiCl_4$ | 0.894 g (5.26 × $10^{-3}$ moles) | |
| (iv) $C_6H_5(CH_3)SiH_2$ | 1.630 g (13.3 × $10^{-3}$ moles) | |

After a reaction time of 1 hour, the reaction mixture had the following composition:

| | | |
|---|---|---|
| (1) $SiH_4$ | 2.86% | |
| (2) $H_3SiCl$ | 3.80% | |
| (3) $H_2SiCl_2$ | 3.84% | |
| (4) $HSiCl_3$ | 2.84% | |
| (5) $SiCl_4$ | 0.54% | |
| (6) $C_6H_5(CH_3)SiH_2$ | 0% | |
| (7) $C_6H_5(CH_3)SiHCl$ | 67.72% | |
| (8) $C_6H_5(CH_3)SiCl_2$ | 18.40% | |

This corresponds to a degree of conversion of $SiCl_4$ of 98% and a degree of conversion of $C_6H_5(CH_3)SiH_2$ of 100%.

EXAMPLE 29

The procedure of the preceding examples was repeated, for redistribution reaction between $SiCl_4$ and $(CH_3)_2SiH(OC_2H_5)$ in the absence of a solvent:

| | | |
|---|---|---|
| (i) TDA 1 | 0.832 g (2.57 × $10^{-3}$ moles) | |
| (ii) LiBr | 74.6 mg (0.85 × $10^{-3}$ moles) | |
| (iii) $SiCl_4$ | 0.726 g (4.12 × $10^{-3}$ moles) | |
| (iv) $(CH_3)_2SiH(OC_2H_5)$ | 0.180 g (1.73 × $10^{-3}$ moles) | |

After a reaction time of 4 hours 30 minutes, the reaction mixture had the following composition:

| | | |
|---|---|---|
| (1) $(CH_3)_2SiHCl$ | 8.38% | |
| (2) $HSiCl_3$ | 14.62% | |
| (3) $(CH_3)_2SiH(OC_2H_5)$ | 0% | |
| (4) $SiCl_4$ | 46.13% | |
| (5) $(CH_3)_2SiCl(OC_2H_5)$ | 14.97% | |
| (6) $C_2H_5OSiCl_3$ | 15.90% | |
| (7) $C_6H_5(CH_3)SiCl_2$ | 18.40% | |

This corresponds to a degree of conversion of $SiCl_4$ of 42% and a degree of conversion of $(CH_3)_2SiH(OC_2H_5)$ of 100%. It will be appreciated that in parallel to the desired reaction which formed $HSiCl_3$, a chlorine-ethoxy exchange reaction took place between the two reaction products, with formation of $(CH_3)_2SiClH$ and $C_2H_5OSiCl_3$.

EXAMPLE 30

This example illustrates the preparation of dichlorosilane by reaction between $HSiCl_3$ and $CH_3SiHCl_2$ in the presence of TDA 1 plus LiBr as the catalyst and $C_6H_5Cl$ as the solvent.

The apparatus used for this experiment was a follows: a jacketed Pyrex ® reactor of about 1 liter capacity, with magnetic stirring, heated by means of a circulatory thermostat. Surmounting this reactor was a column packed with Fenske rings, which in turn was surmounted by an upright condenser for condensing the chlorosilanes, which are less volatile than $H_2SiCl_2$, and which can be entrained by the latter. This condenser was cooled to 5°-8° C.

The dichlorosilane produced was recovered by bubbling through chlorobenzene cooled to −30° C.

The entire apparatus was rendered inert by charging same with argon before the reactants were introduced.

The following reaction mixture was employed (the various compounds were introduced in the order noted below):

| | | |
|---|---|---|
| (i) Chlorobenzene | 4 mols, i.e., 450 g | |
| (ii) TDA 1 | 1 mol, i.e., 323 g | |
| (iii) LiBr | 0.165 mol, i.e., 14.3 g | |

The reaction mixture was stirred until the salt had completely dissolved and it was then heated to 70° C. before gradual introduction of the silanes, namely:

| | | |
|---|---|---|
| | $CH_3SiHCl_2$ | 1 mol, i.e., 115 g |
| followed by | $HSiCl_3$ | 1 mol, i.e., 135 g |

The $H_2SiCl_2$ formed was evolved immediately (the reaction mixture being at boil).

According to the amount of $H_2SiCl_2$ obtained and the amount of $CH_3SiCl_3$ formed (chromatographic analyses of the reaction mixture), the time required to reach 50% conversion of the reactants was 9 minutes.

Total duration of experiment: 6 hours.

Upon completion of the experiment, the temperature of the reaction mixture was 80° C. and the degree of conversion of $CH_3SiHCl_2$ was 80%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of a hydrogenosilane, comprising redistributing (1) a silane having the formula $H_mSiX_{4-m}$ in which X is halogen or an alkoxy group and m is an integer equal to 0, 1, 2 or 3, by reacting said silane with (2) an alkyl or aryl hydrogenosilane having the formula $R_nH_pSiX'_{4-(n+p)}$ in which X' is halogen or an alkoxy group, R is at least one alkyl or aryl group, which may be identical or different, and n and p, which may be identical or different, are integers equal to 1, 2 or 3, with the proviso that $n+p \leq 4$, in the presence of (3) a catalytically effective amount of a catalyst system which comprises (i) at least one ionic inorganic salt having the formula $M^+A^-$ and (ii) a compound which complexes the $M^+$ cation of said salt (i) and at least partially solubilizes and dissociates same in the medium of reaction.

2. The process as defined by claim 1, wherein said ionic inorganic salt (i), $M^+$ comprises an alkali metal, an alkaline earth metal, or ammonium, and $A^-$ comprises a halogen, $SCN^-$, $CN^-$ or $CO_3^=$.

3. The process as defined by claim 2, wherein $M^+$ comprises $Li^+$, $Na^+$, $K^+$, $Ca^{++}$ or $NH_4^+$, and $A^-$ comprises $Cl^-$, $Br^-$ or $I^-$.

4. The process as defined by claim 1, wherein the compound (ii) complexing the cation of the ionic inorganic salt (i) comprises a sequestering agent of the formula:

$$[N—(CHR_1—CHR_2—O—(CHR_3—CHR_4—O)_{n}—R_5)_3] \quad (I)$$

in which n is an integer greater than or equal to 0 and less than or equal to 10 ($0 \leq n \leq 10$), $R_1$, $R_2$, $R_3$ and $R_4$, which may be identical or different, are each a hydrogen atom or an alkyl radical containing from 1 to 4 carbon atoms and $R_5$ is an alkyl or cycloalkyl radical containing from 1 to 12 carbon atoms, a phenyl radical or a $—C_mH_{2m}—\phi$ or $C_mH_{2m+1}—\phi—$ radical, wherein m ranges from 1 to 12 ($1 \leq m \leq 12$) and $\phi$ is benzene.

5. The process as defined by claim 1, wherein the complexing compound (ii) comprises a macrocyclic polyether containing from 15 to 30 ring atoms and 4 to 10 10—O—X units, in which X is $—CHR_6—CHR_7—$ or $—CHR_6—CHR_8—CR_9R_7—$, wherein $R_6$, $R_7$, $R_8$ and $R_9$, which may be identical or different, are each a hydrogen atom or an alkyl radical containing from 1 to 4 carbon atoms, and wherein one of the symbols X may be $—CHR_6—CHR_8—CR_9R_7—$ when the —O—X units comprise —O—$CHR_6—CHR_7$.

6. The process as defined by claim 1, wherein the complexing compound (ii) comprises a macrocyclic or dicyclic compound of the general formula IIa or IIb:

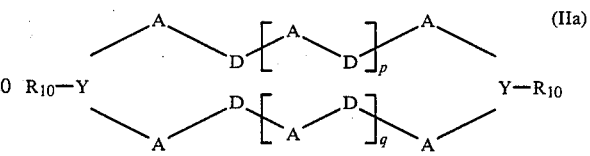
(IIa)

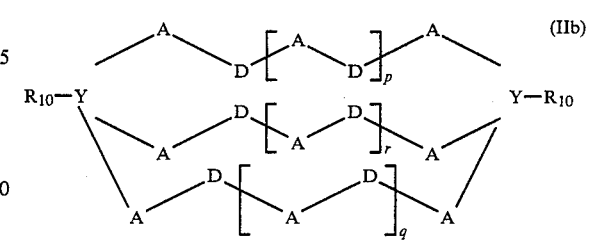
(IIb)

wherein Y is N or P, A is an alkylene group containing from 1 to 3 carbon atoms, D is O, S or $N—R_{11}$ where $R_{11}$ is an alkyl radical containing from 1 to 6 carbon atoms, $R_{10}$ is an alkyl radical containing from 1 to 6 carbon atoms, and p, q and r, which may be identical or different, are integers ranging from 1 to 5.

7. The process as defined by any of claims 4, 5 or 6, wherein said complexing compound (ii) comprises said sequestering agents, macrocyclic polyethers, macrocyclic or dicyclic compounds grafted onto a crosslinked organic polymer support.

8. The process as defined by claim 7, wherein said complexing compound (ii) comprises sequestering agent radicals of the general formula:

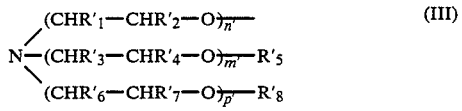
(III)

in which $R_1'$, $R_2'$, $R_3'$, $R_4'$, $R_6'$ and $R_7'$, which may be identical or different, are each a hydrogen atom or an alkyl radical containing from 1 to 4 carbon atoms, $R_5'$ and $R_8'$, which may be identical or different, are each a hydrogen atom, an alkyl or cycloalkyl radical containing from 1 to 12 carbon atoms, a phenyl radical, a $—C_{q'}H_{2q'}—\phi—$ or $C_{q'}H_{2q'+1}—\phi—$ radical, wherein $\phi$ is benzene, q' is greater than or equal to 1, and n', m', and p', which may be identical or different, are each greater than or equal to 1 and less than or equal to 10.

9. The process as defined by claim 4, wherein the sequestering agent of the formula (I) comprises:

(i) tris(3-oxabutyl)amine of the formula:

N—CH₂—CH₂—O—CH₃)₃

(ii) tris(3,6-dioxaheptyl)amine of the formula:

N—CH₂—CH₂—O—CH₂—CH₂—O—CH₃)₃

(iii) tris(3,6,9-trioxadecyl)amine of the formula:

N—CH₂—CH₂—O—CH₂—CH₂—O—CH₂—CH₂—O—CH₃)₃

(iv) tris(3,6-dioxaoctyl)amine of the formula:

N—CH₂—CH₂—O—CH₂—CH₂—C₂H₅)₃

(v) tris(3,6,9-trioxaundecyl)amine of the formula:

N—CH₂—CH₂—O—CH₂—CH₂—O—CH₂—CH₂—O—C₂H₅)₃

(vi) tris(3,6-dioxanonyl)amine of the formula:

N—CH₂—CH₂—O—CH₂—CH₂—O—C₃H₇)₃

(vii) tris(3,6,9-trioxadodecyl)amine of the formula:

N—(CH₂—CH₂—O—CH₂—CH₂—O—CH₂—CH₂—O—C₃H₇)₃

(viii) tris(3,6-dioxadecyl)amine of the formula:

N—CH₂—CH₂—O—CH₂—CH₂—O—C₄H₉)₃

(ix) tris(3,6,9-trioxatridecyl)amine of the formula:

N—CH₂—CH₂—O—CH₂—CH₂—O—CH₂—CH₂—O—C₄H₉)₃

(x) tris(3,6,9,12-tetraoxatridecyl)amine of the formula:

N—CH₂—CH₂—O—CH₂—CH₂—O)₃—CH₃)₃

(xi) tris(3,6,9,12,15,18-hexaoxanonadecyl)amine of the formula:

N—CH₂—CH₂—O—(CH₂—CH₂—O—₅CH₃)₃

(xii) tris(3,6-dioxa-4-methylheptyl)amine of the formula:

N—CH₂—CH₂—OCH—(CH₃)—CH₂—O—CH₃)₃

(xiii) tris(3,6-dioxa-2,4-dimethylheptyl)amine of the formula:

N—CH₂—CH—(CH₃)—OCH(CH₃)—CH₂—O—CH₃)₃.

10. The process as defined by claim 5, wherein said macrocyclic polyether comprises a compound of the general formula:

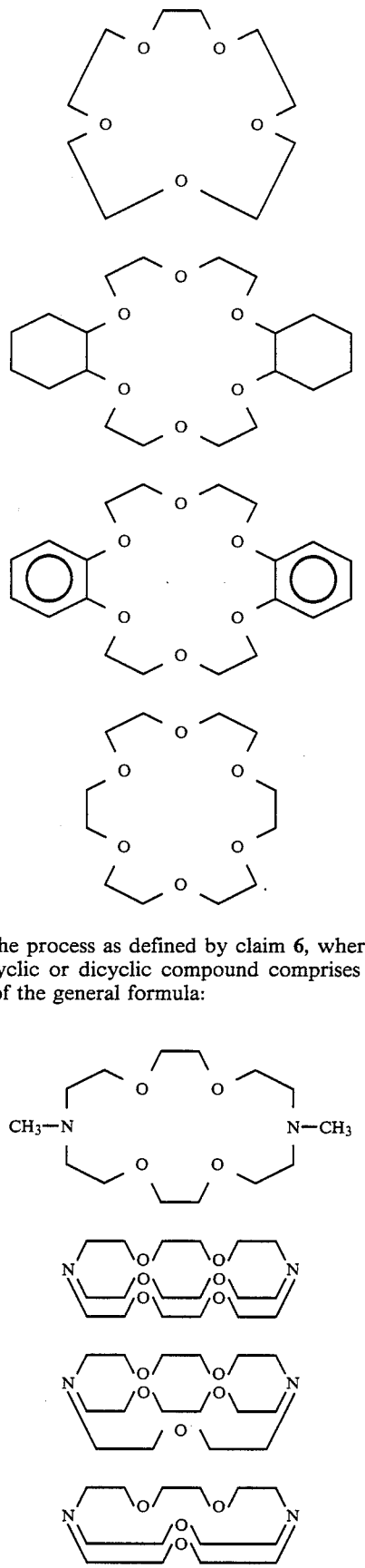

11. The process as defined by claim 6, wherein said macrocyclic or dicyclic compound comprises a compound of the general formula:

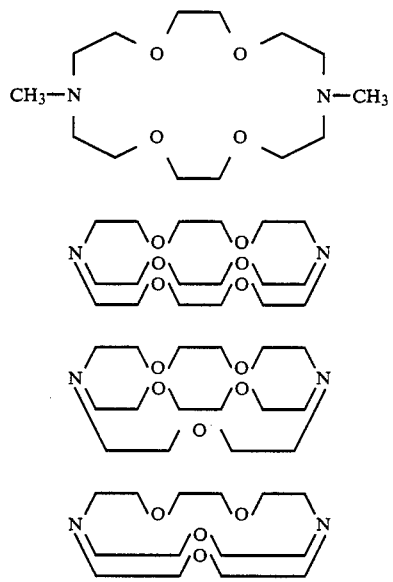

-continued

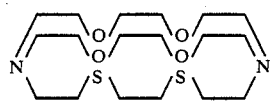

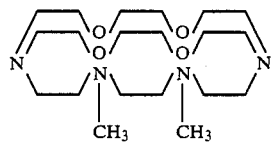

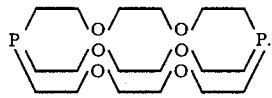

12. The process as defined by claim 8, wherein said radicals of the formula (III) comprise:

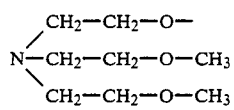

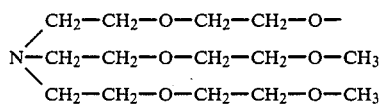

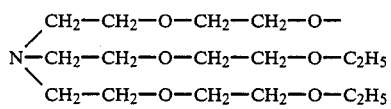

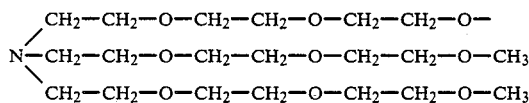

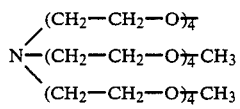

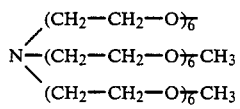

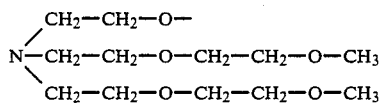

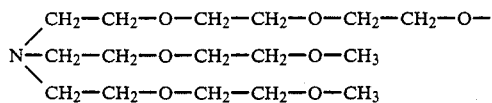

-continued

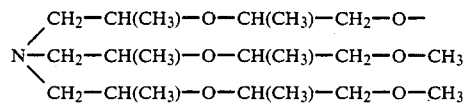

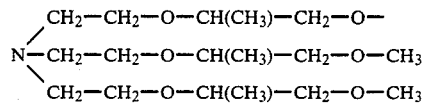

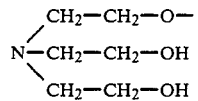

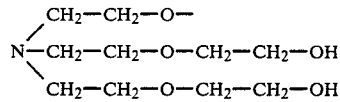

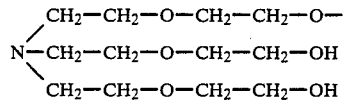

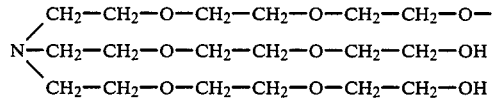

or

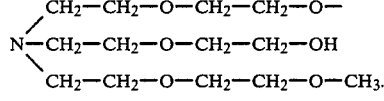

13. The process as defined by claim 7, wherein said organic polymer comprises a polymer of a vinylaromatic compound or a copolymer of a vinylaromatic compound with a $C_4$-$C_6$ conjugated diene.

14. The process as defined by claim 1, wherein the molar ratio of the complexing compound (ii) to the ionic inorganic salt (i) ranges from 0.05 to 100.

15. The process as defined by claim 14, wherein said ratio ranges from 0.5 to 5.

16. The process as defined by claim 14, wherein the molar ratio of the ionic inorganic salt (i) to the silane starting materials ranges from 10 to 0.0001.

17. The process as defined by claim 16, wherein said ratio ranges from 0.5 to 0.0001.

18. The process as defined by claim 1, said silane (1) comprising tetrachlorosilane, trichlorosilane, dichlorosilane, or admixture thereof.

19. The process as defined by claim 18, said hydrogenosilane (2) comprising methylsilane, methylchlorosilane, dimethylchlorosilane, methyldichlorosilane, dimethylsilane, trimethylsilane, phenyldichlorosilane, phenylchlorosilane, diphenylchlorosilane, ethyldichlorosilane, methylphenylchlorosilane, methylphenylsilane, or admixture thereof.

20. The process as defined by claim 1, carried out in the presence of a reaction solvent.

* * * * *

UNITED STATES PATENT AND TRADEMARK OFFICE
CERTIFICATE OF CORRECTION

PATENT NO.  : 4,567,286
DATED       : January 28, 1986
INVENTOR(S) : Jean-Luc LEPAGE and Gerard SOULA It is certified that error appears in the above-identified patent and that said Letters Patent is hereby corrected as shown below:

Please change the title from "PREPARATION OF HYDROGENATED SILANES BY REDISTRIBUTION OF HYDROSILANES" to read --PREPARATION OF HYDROGENOSILANES BY REDISTRIBUTION--.

Signed and Sealed this

Twenty-second Day of September, 1987

Attest:

DONALD J. QUIGG

Attesting Officer     Commissioner of Patents and Trademarks